US012661522B2

(12) United States Patent
Wasserman et al.

(10) Patent No.: US 12,661,522 B2
(45) Date of Patent: Jun. 23, 2026

(54) TRANSDUCER APPARATUSES WITH ELECTRODE ELEMENT SPACING TO REDUCE EDGE EFFECT IN DELIVERING TUMOR TREATING FIELDS TO A SUBJECT'S BODY

(71) Applicant: Novocure GmbH, Root (CH)

(72) Inventors: Yoram Wasserman, Haifa (IL); Stas Obuchovsky, Haifa (IL); Nataliya Kuplennik, Haifa (IL); David Shapiro, Haifa (IL); Elie Yaacobi, Haifa (IL); Golan Bar-Tal, Haifa (IL); Noa Halavee, Tel Aviv (IL)

(73) Assignee: Novocure GmbH, Baar (CH)

( * ) Notice: Subject to any disclaimer, the term of this patent is extended or adjusted under 35 U.S.C. 154(b) by 639 days.

(21) Appl. No.: 17/886,319

(22) Filed: Aug. 11, 2022

(65) Prior Publication Data

US 2023/0046799 A1 Feb. 16, 2023

Related U.S. Application Data

(63) Continuation of application No. 17/698,457, filed on Mar. 18, 2022.

(Continued)

(51) Int. Cl.
*A61N 1/40* (2006.01)
*A61N 1/36* (2006.01)

(52) U.S. Cl.
CPC ........... *A61N 1/40* (2013.01); *A61N 1/36002* (2017.08)

(58) Field of Classification Search
CPC ................ A61N 1/0456; A61N 1/0492; A61N 1/36014; A61N 1/0484; A61N 1/0476; A61N 1/36002; A61N 5/0616
See application file for complete search history.

(56) References Cited

U.S. PATENT DOCUMENTS

| 7,565,205 B2 | 7/2009 | Palti | |
| 8,244,345 B2 * | 8/2012 | Palti | ........................ A61N 1/40 |
| | | | 607/2 |

(Continued)

FOREIGN PATENT DOCUMENTS

| JP | 2012-143590 A | 8/2012 |
| JP | 2021-514208 A | 6/2021 |
| WO | WO-2019/136176 A1 | 7/2019 |

OTHER PUBLICATIONS

International Search Report issued in International Application No. PCT/IB2022/057577 dated Mar. 24, 2023.

*Primary Examiner* — Benjamin J Klein
*Assistant Examiner* — Daniel Tehrani
(74) *Attorney, Agent, or Firm* — McCarter & English, LLP; Michael A. Sartori

(57) ABSTRACT

A transducer apparatus for delivering tumor treating fields to a subject's body, the transducer apparatus including: a plurality of electrode elements; wherein the plurality of electrode elements comprises a first electrode element and a second electrode element, wherein the first electrode element and the second electrode element are substantially located in a plane of the transducer apparatus; and when viewed from a direction perpendicular to the plane, the first electrode element and the second electrode element have edges located adjacent each other without any other electrodes between them, wherein the edges of the first electrode element and the second electrode element extend parallel to each other along their length.

20 Claims, 7 Drawing Sheets
(1 of 7 Drawing Sheet(s) Filed in Color)

Related U.S. Application Data

(60) Provisional application No. 63/232,229, filed on Aug. 12, 2021, provisional application No. 63/232,329, filed on Aug. 12, 2021.

(56) References Cited

U.S. PATENT DOCUMENTS

| | | | |
|---|---|---|---|
| 2013/0008026 A1* | 1/2013 | Walter | A61N 1/0553 |
| | | | 29/874 |
| 2013/0190847 A1* | 7/2013 | Palti | A61N 1/0408 |
| | | | 607/115 |
| 2017/0216593 A1 | 8/2017 | Lee | |
| 2019/0022372 A1* | 1/2019 | Dar | A61N 1/0484 |
| 2019/0133673 A1 | 5/2019 | Boll et al. | |
| 2020/0078582 A1* | 3/2020 | Alon | A61N 1/32 |
| 2020/0171297 A1 | 6/2020 | Kirson et al. | |
| 2021/0023366 A1* | 1/2021 | Ramos Macias | A61N 1/36036 |
| 2021/0185975 A1 | 6/2021 | Strauss et al. | |
| 2021/0220640 A1 | 7/2021 | Deslauriers | |
| 2022/0305276 A1 | 9/2022 | Marciano et al. | |

* cited by examiner

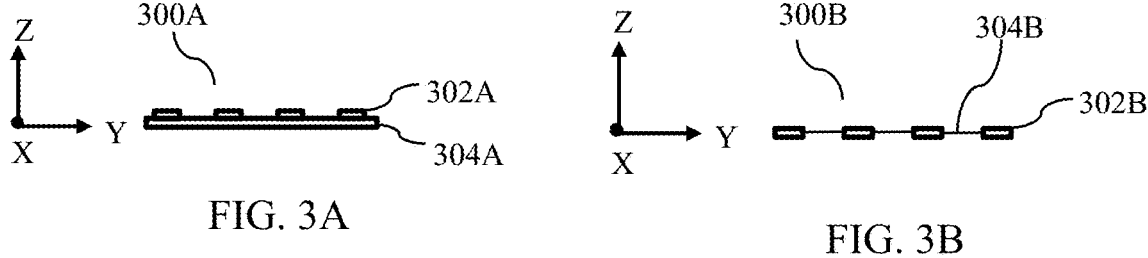
FIG. 3A
FIG. 3B
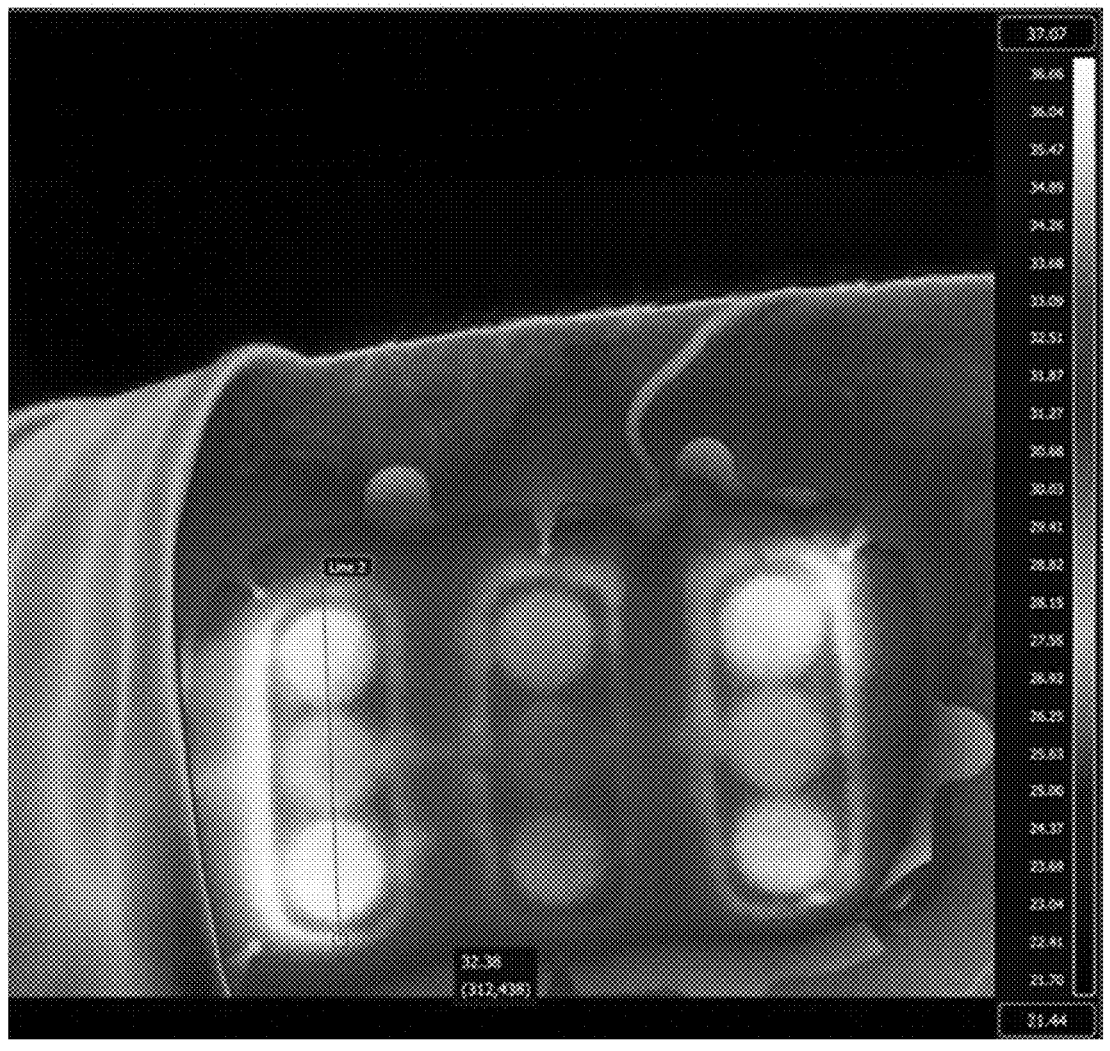
FIG. 3C

TRANSDUCER APPARATUSES WITH ELECTRODE ELEMENT SPACING TO REDUCE EDGE EFFECT IN DELIVERING TUMOR TREATING FIELDS TO A SUBJECT'S BODY

CROSS REFERENCE TO RELATED APPLICATIONS

This application claims priority to U.S. patent application Ser. No. 17/698,457 filed Mar. 18, 2022, U.S. Patent Application No. 63/232,329 filed Aug. 12, 2021, and U.S. Patent Application No. 63/232,229 filed Aug. 12, 2021, all of which are incorporated herein by reference.

BACKGROUND

Tumor treating fields (TTFields) are low intensity (e.g., 1-4 V/cm) alternating electric fields within the intermediate frequency range (e.g., 50 kHz to 1 MHz, such as 50-550 kHz), which may be used to treat tumors as described in U.S. Pat. No. 7,565,205. TTFields therapy is an approved mono-treatment for recurrent glioblastoma (GBM) and an approved combination therapy with chemotherapy for newly diagnosed GBM patients. TTFields can also be used to treat tumors in other parts of a subject's body (e.g., lungs, ovaries, pancreas). For example, TTFields therapy is an approved combination therapy with chemotherapy for malignant pleural mesothelioma (MPM). TTFields are induced non-invasively into the region of interest by transducers (e.g., arrays of capacitively coupled electrode elements) placed directly on the patient's body (e.g., using the Novocure Optune™ system), and applying AC voltages between the transducers.

Conventional transducers used to generate TTFields include a plurality of ceramic disks. One side of each ceramic disk is positioned against the patient's skin, and the other side of each disc has a conductive backing. Electrical signals are applied to this conductive backing, and these signals are capacitively coupled into the patient's body through the ceramic discs. Conventional transducer designs include rectangular arrays of ceramic disks aligned with each other in straight rows and columns (e.g., in a three-by-three arrangement).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A and 3B depict cross-sectional views of examples of the structure of various transducers.

FIG. 3C depicts a thermal image of a rectangular electrode array.

Various embodiments are described in detail below with reference to the accompanying drawings, wherein like reference numerals represent like elements.

DESCRIPTION OF EMBODIMENTS

Figure 1:
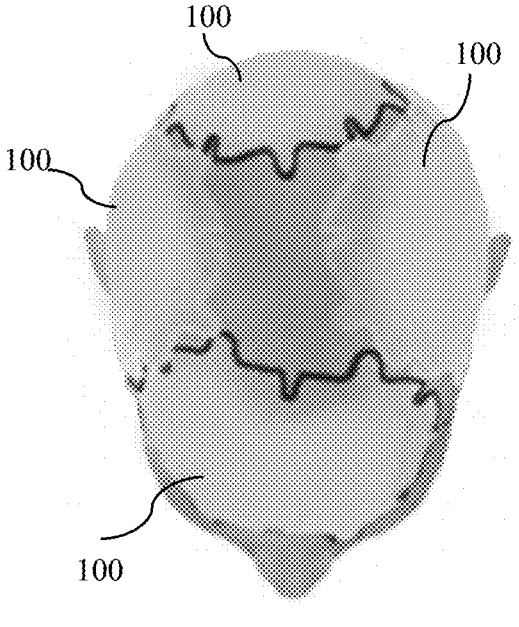
FIG. 1 depicts an example of transducers located on a subject's head.

This application describes exemplary transducer apparatuses for delivering TTFields to a subject's body and used to treat one or more cancers located in the subject's body.

When TTFields are applied to a subject's body, the temperature at the subject's body may increase proportionally to the induced electric field. Regulations limit the amount of current that can be driven through a transducer to an amount that keeps the measured temperature at locations on the subject's body below a temperature threshold. As practiced in the art, the temperature at the location of the transducers on the subject's body is controlled to be below the temperature threshold by reducing the operational current driven by the transducer and reducing the strength of the resulting TTFields. This in turn becomes an over-riding limitation on the TTFields strength that can be used to treat the tumor. Accordingly, there is a need in the art to safely access higher TTField strengths without exceeding the temperature threshold at the subject's skin.

The inventors have discovered that, on a transducer comprising an array of electrode elements, the electrode elements located along the edge of the array have a lower resistance to current flowing therethrough compared to the electrode elements located toward the middle of the array. This can lead to higher concentrations of electric charge at points on the edge (e.g., outer perimeter) of the array in general. Further, an electrode element located at a corner or similar sharp bend in the edge of the array will have a higher concentration than other electrode elements along the edge and in the center of the array. The tendency of a transducer to drive higher amounts of current through electrode elements located along the edge of the array, and particularly at the corners, is referred to herein as the "edge effect."

An uneven distribution of current through the array of a transducer due to the edge effect can lead to higher temperature zones (or "hot spots") forming at distant corners and along edges of the array. These hot spots are the locations that reach the threshold temperature first and therefore control the requirement to reduce the current. As such, the generation of hot spots due to the edge effect limits the maximum operational current that may be driven by a transducer, and the strength of the resulting TTFields.

The inventors have now recognized that a need exists for transducers having electrode element array layouts that reduce or minimize the edge effect and allow the application of higher operating currents to the transducers. Transducers operated with increased current can induce stronger TTFields in the subject's body, ultimately leading to better patient outcomes. Each of the disclosed transducer apparatuses have an array of electrode elements positioned in a layout and having shapes that reduce or minimize the edge effect.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an" and "the" include plural referents unless the context clearly dictates otherwise.

FIG. 1 depicts transducers 100 positioned on the head of a subject's body. FIG. 1 depicts one example of a subject's head on which transducers 100 are placed in various positions and/or orientations. Such an arrangement of transducers 100 on a subject's head is capable of applying TTFields to a tumor in a region of the subject's brain. It should be noted that various other positions and/or orientations on the subject's head may be selected for placement of transducers.

Each transducer 100 may have an array of electrode elements disposed thereon as described herein. Each transducer 100 may be placed on a subject's head with a face of the array of electrode elements facing the subject's head. A transducer 100 may be placed on the subject's head such that the face of the array of electrode elements conforms to the head's outer shape.

Figure 2:
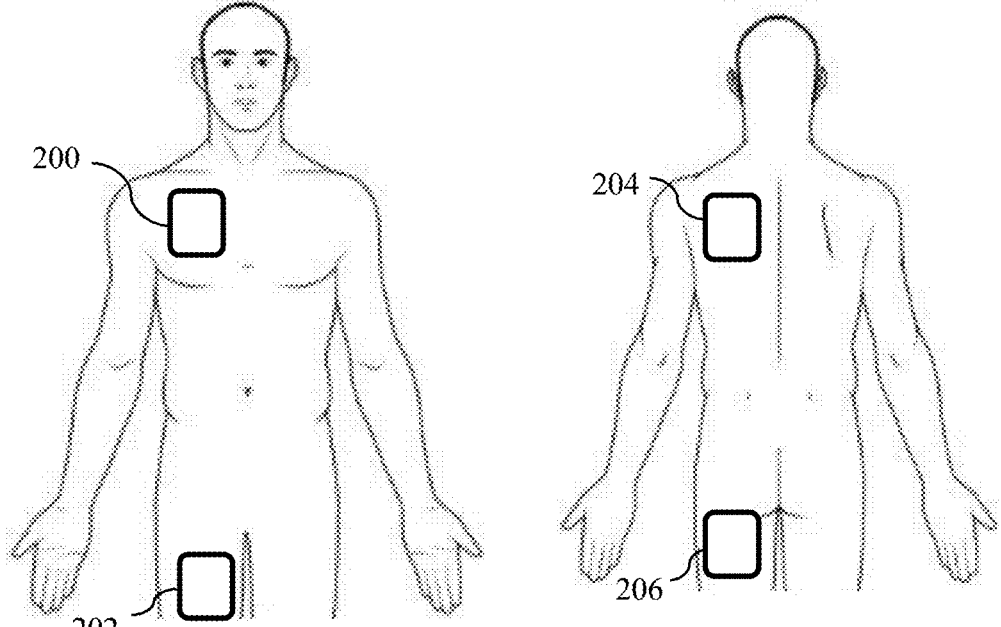
FIG. 2 depicts an example of transducers located on a subject's torso.

FIG. 2 depicts transducers 200, 202, 204, and 206 attached to a subject's body for applying TTFields to the torso of the subject's body. In one embodiment, two electric fields are alternatively applied between two pairs of transducers. Each pair of transducers corresponds to a channel for generating TTFields in the subject's body. In the example depicted in FIG. 2, transducer 200 is attached to the front of the subject's right chest, transducer 202 is attached to the front of the subject's right thigh, transducer 204 is attached to the back of the subject's left chest, and transducer 206 is attached to the back of the subject's left thigh. As for pairs of transducers, the transducers 200 and 206 may form a first pair of transducers, and the transducers 202 and 204 may form a second pair of transducers.

FIG. 2 depicts the transducers 200, 202, 204, and 206 attached to the subject's body. As an example, the transducers 200, 202, 204, and 206 may be affixed to the subject's body by applying a medically appropriate glue onto a surface of each transducer. In other embodiments, the transducers 200, 202, 204, and 206 may be placed in alternative positions on the body. In other embodiments, the transducers 200, 202, 204, and 206 may be attached to one or more garments (not shown) such as, for example, a shirt and pants. In an example, the transducers 200, 202, 204, and 206 may be attached to clothes using adhesive. In another example, the transducers 200, 202, 204, and 206 may be attached to clothes by incorporating the transducers 200, 202, 204, and 206 within the clothing. In examples where transducers are disposed at locations on the subject's head, the corresponding transducers may be integrated in another type of garment (e.g., hat).

Each of the transducers 200, 202, 204, and 206 may have an array of electrode elements disposed thereon as described herein. Each transducer 200, 202, 204, and 206 may be placed over the subject's body with a face of the array of electrode elements facing the subject's body. The transducers 200, 202, 204, and 206 may be placed on the subject's body such that the face of the corresponding array of electrode elements conforms to the outer shape of the subject's body.

The arrays of electrode elements may include a number of different layouts and/or electrode element geometries disclosed herein that reduce or minimize the edge effect during operation of the transducer. The layouts may include, for example: adjacent first and second electrode elements having parallel edges; adjacent first and second electrode elements that are non-circular and having a changing distance between their adjacent edges; a separation between two groups of electrode elements in the array of electrode elements; electrode elements having a first edge and a second edge extending radially outward from a center portion of the array and a rounded edge connecting the first and second edges; and/or electrode elements having a larger area thereof located closer to an outer edge of the array than to a center portion of the array.

FIGS. 3A and 3B depict cross-sectional views of examples of the structure of a transducer. For example, as shown in FIG. 3A, the transducer 300A has a plurality of electrode elements 302A and a substrate 304A. The substrate 304A is configured for attaching the transducer 300A to a subject's body. Suitable materials for the substrate 304A include, for example, cloth, foam, and flexible plastic. In one example, the substrate 304A includes a conductive medical gel having a thickness of not less than approximately 0.5 mm. In a more specific example, the substrate 304A is a layer of hydrogel with a minimum thickness of 0.5 mm. In this situation, the transducer 300A is attached to the subject's body through the substrate 304A.

A plurality of electrode elements 302A are positioned on the substrate 304A. Each of the electrode elements may have a conductive plate with a dielectric layer disposed thereon that faces towards the substrate 304A. Optionally, one or more sensors may be positioned beneath each of the electrode elements 302A in a manner that is similar to the conventional arrangement used in the Novocure Optune® system. In one example, the one or more sensors are temperature sensors (e.g., thermistors).

FIG. 3B depicts a cross-sectional view of another example of the structure of the transducer 300B. In this example, the transducer 300B includes a plurality of electrode elements 302B. The plurality of electrode elements 302B are electrically and mechanically connected to one another without a substrate. The electrode elements 302B may be connected through conductive wires 304B.

As depicted in FIGS. 3A and 3B, the transducers 300A and 300B comprise arrays of substantially flat electrode elements 302A and 302B, respectively. In each of FIGS. 3A and 3B, the array of electrode elements may be capacitively coupled. In some embodiments, the electrode elements 302A and 302B are non-ceramic dielectric materials positioned over a plurality of flat conductors. Examples of non-ceramic dielectric materials positioned over flat conductors include polymer films disposed over pads on a printed circuit board or over substantially planar pieces of metal. In other embodiments, the electrode elements 302A and 302B are ceramic elements.

Transducers that use an array of electrode elements that are not capacitively coupled may also be used. In this situation, each electrode element 302A and 302B may be implemented using a region of a conductive material that is configured for placement against a subject's body, with no insulating dielectric layer between the conductive elements and the body.

Other alternative constructions for implementing the transducer for use with embodiments of the invention may also be used, as long as they are capable of (a) delivering TTFields to the subject's body and (b) being positioned at locations of the subject's body.

FIGS. 3A and 3B depict the transducers 300A and 300B from a direction perpendicular to a Y-Z plane defined by a 3-dimensional coordinate axis shown in the figures. As illustrated, the electrode elements 302A and 302B are distributed along a direction parallel to the Y-axis. In addition, the electrode elements 302A and 302B may be distributed along a direction parallel to the X-axis. As such, the transducers 300A and 300B may each comprise an array of electrode elements 302A and 302B, respectively, distributed along a face of the array and substantially located in a plane parallel to the X-Y plane. The face of the array (parallel to the X-Y plane) is configured to face the subject's body when the transducer is positioned over the subject's body. Similar 3-dimensional coordinate axes are depicted in the remaining figures.

FIG. 3C depicts a thermal heat map of a 9-electrode transducer array (3×3 rectangular array of electrodes) in use, which illustrates the presence of higher temperature zones, or "hot-spots", along the edges, and particularly at the corners of the array. As discussed above, the generation of hot spots due to the edge effect limits the maximum operational current that may be driven by a transducer, and the strength of the resulting TTFields.

FIGS. 4-11 each depict example layouts of electrode elements on a transducer, in accordance with disclosed embodiments. In each example layout of electrode elements described herein (e.g., in FIGS. 4-11), the layout is viewed from a direction perpendicular to the face (i.e., perpendicular to the X-Y plane) of the array of electrode elements. The array of electrode elements is configured to be positioned over the subject's body with this face of the array facing the subject's body. In the example layouts described herein, the "array of electrode elements" may comprise all electrode elements (e.g., 402A-402H in FIG. 4) present on the transducer apparatus (e.g., 400 in FIG. 4).

As depicted in FIGS. 4-11, the transducer (e.g., 400 in FIG. 4) may include a substrate (e.g., 404 in FIG. 4) on which the electrode elements are disposed. In some embodiments (e.g., FIGS. 4 and 5), the substrate may have cuts, slits, or perforations formed therein to facilitate placement of the substrate over rounded edges of a subject's body. As discussed above, other embodiments of the transducer may not include a substrate. The disclosed electrode element layouts may be equally applied to transducers in which a substrate is present and to transducers where no substrate is present.

In certain transducers, for example as depicted in FIGS. 6A-11, at least one of the electrode elements in the array is extending from a central portion of the array toward an outer periphery of the array. In certain transducers, for example as depicted in FIGS. 4-9, each electrode element in the array may have approximately the same surface area. In certain transducers described herein, there are embodiments for which each electrode element in the array may have approximately the same size and/or shape. In other embodiments, one or more electrode element in the array may differ in size and/or shape from the other electrode elements.

In the following description of FIGS. 4-11, reference is made to individual electrode elements having one or more edges. The term "edge" used herein refers to at least a portion of the external boundary of the electrode element when viewed from the direction perpendicular to the X-Y plane. The "edge" has a length. Therefore, the "edge" is not simply a point on the external boundary of the electrode element.

Each electrode element layout described herein (e.g., in FIGS. 4-11) is designed to reduce or minimize the edge effect and reduce the presence or intensity of hot spots formed by the array of electrode elements. This may be accomplished by manipulating the geometry and/or placement of the electrode elements of the array, and more particularly the spacing between electrode elements of the array to promote substantially uniform shielding between electrode elements. The term "shielding" refers to an increase in resistance to current flow through an electrode element brought on by the presence of one or more neighboring electrode elements. Promoting uniform shielding between all electrode elements in an array may balance the current output from the electrodes such that the current is relatively consistent across the array. This allows for increasing the current supplied to the transducer while maintaining temperatures on the subject's body below a threshold temperature.

Figure 4:
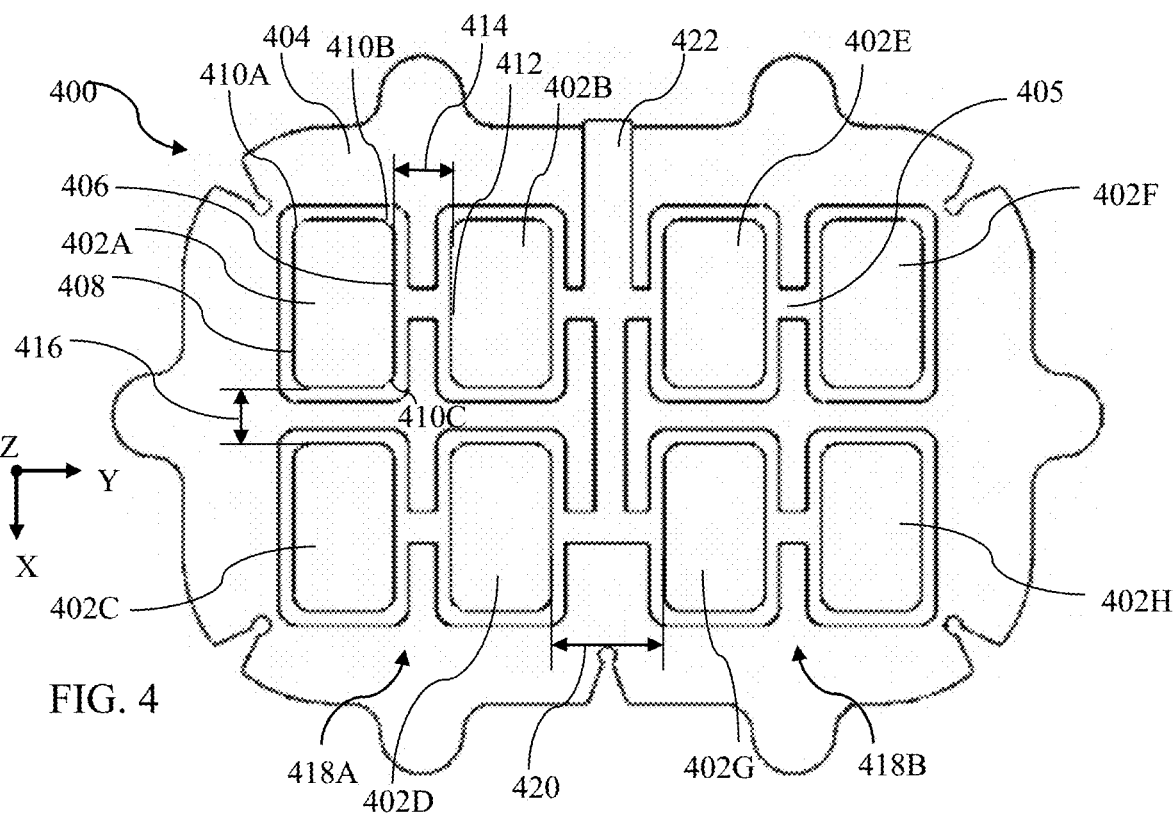
FIG. 4 depicts an example layout of an array of electrode elements on a transducer apparatus.
Figure 5:
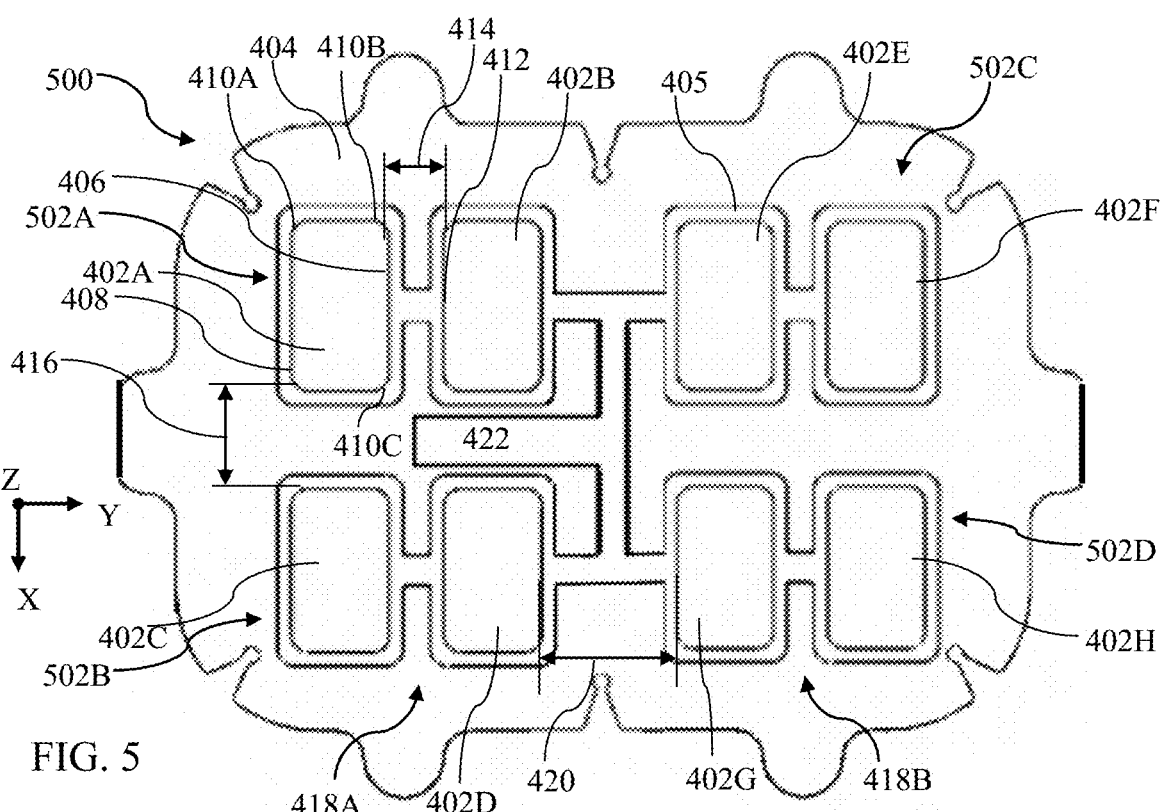
FIG. 5 depicts another example layout of an array of electrode elements on a transducer apparatus.

FIG. 4 depicts a transducer 400 with an example layout of electrode elements 402, which may be disposed on a substrate 404. As illustrated, the electrode elements 402 of the transducer 400 may be electrically coupled to each other. In FIG. 4, the transducer's array of electrode elements comprises eight electrode elements 402A-402H. FIG. 5 depicts a transducer 500 with another example layout of electrode elements 402. The layout in FIG. 5 includes similar features to those of FIG. 4, as described herein.

FIGS. 4 and 5 depict a layered structure of the transducers 400 and 500. As shown, the transducers 400 and 500 may include a printed circuit board (PCB) layer 405 between the electrode elements 402 and the substrate 404. The PCB layer 405 may include conductive pathways that electrically couple the electrode elements 402 together.

Certain shapes of the individual electrode elements 402 may help balance the current through the array. In an example, at least one of the electrode elements 402 in the array may have a square, rectangular, or hexagonal shape or a substantially square, rectangular, or hexagonal shape with one or more rounded corners. FIGS. 4 and 5 depict each electrode element 402 having a substantially rectangular shape with four rounded corners. As illustrated with reference to the electrode element 402A, one or more electrode elements 402 may comprise: a first edge 406, a second edge 408, and at least one rounded edge (e.g., rounded corners 410A and 410B) connecting the first edge 406 to the second edge 408 at an end of the electrode element 402A. As depicted, the first edge 406 and the second edge 408 of the electrode element 402A are substantially parallel (e.g., within ±5 degrees).

As mentioned above, controlling the spacing between individual electrode elements 402 may help balance the current through the array. In an example, a first electrode element (e.g., 402A) and a second electrode element (e.g., 402B) each have edges located adjacent each other without any other electrodes between them. For example, the first edge 406 of the electrode element 402A is located adjacent an edge 412 of the electrode element 402B. The first edge 406, as shown, may be a substantially straight edge portion of the electrode element 402A located between two rounded corners 410B and 410C of the electrode element 402A. Similarly, the second edge 412 may be a substantially straight edge portion of the electrode element 402B located between two rounded corners of the electrode element 402B. As depicted, the edge 406 of the first electrode element 402A and the edge 412 of the second electrode element 402B extend parallel to each other along their length. Thus, the electrode elements 402A and 402B have a uniform distance 414 therebetween along the length of opposing edges 406 and 412. Having a uniform distance 414 between two electrodes may help balance the current between the electrode elements 402, thereby reducing the edge effect on the transducer.

As depicted, the edge 406 of the electrode element 402A may have a length that is greater than 5% of a total perimeter of the electrode element 402A. More particularly, the edge 406 may have a length that is greater than 10% of the perimeter, greater than 20% of the perimeter, or greater than 25% of the perimeter of the electrode element 402A. Similarly, the edge 412 of the electrode element 402B may have a length that is greater than 5% of the perimeter of the electrode element 402B. More particularly, the edge 412 may have a length that is greater than 10%, greater than 20%, or greater than 25% of the perimeter of the electrode element 402B. This facilitates mutual shielding of the electrode elements 402A and 402B along a sufficiently large section of the electrode elements.

As depicted, an electrode element (e.g., 402A) may have multiple edges that are each parallel to a different adjacent electrode element (e.g., 402B and 402C). For example, in FIGS. 4 and 5 the electrode element 402A has another substantially straight edge that is parallel to and located a uniform distance 416 from a substantially straight edge of the electrode element 402C. In an example shown in FIG. 4, the distance 416 between edges of the electrode elements 402A and 402C may be equivalent or substantially equivalent to the distance 414 between edges of the electrode elements 402A and 402B. In another example shown in FIG. 5, the distances 414 and 416 are different.

The arrangement of electrode elements 402 on the transducer 400/500 depicted in FIGS. 4 and 5 may also contribute to improved current distribution between electrode elements 402. As illustrated, the transducers 400 and 500 each include an array of eight electrode elements 402. Among the eight electrode elements 402, the array may include a first group 418A of four electrode elements 402A-402D arranged in a 2×2 grid pattern and a second group 418B of four electrode elements 402E-402H arranged in a 2×2 grid pattern. As depicted, each 2×2 grid pattern may include first and second electrode elements (e.g., 402A and 402B) being aligned with each other in a direction parallel to the Y-axis, third and fourth electrode elements (e.g., 402C and 402D) being aligned with each other in a direction parallel to the Y-axis, first and third electrode elements (e.g., 402A and 402C) being aligned with each other in a direction parallel to the X-axis, and second and fourth electrode elements (e.g., 402B and 402D) being aligned with each other in a direction parallel to the X-axis. The distance 414 between the first and second electrode elements (e.g., 402A and 402B) may be equivalent to a distance between the third and fourth electrode elements (e.g., 402C and 402D). In addition, the distance 416 between the first and third electrode elements (e.g., 402A and 402C) may be equivalent to a distance between the second and fourth electrode elements (e.g., 402B and 402D). Both groups 418A and 418B may have equivalent sizes and arrangements of the four electrode elements therein.

As depicted, the first group 418A of four electrode elements 402A-402D is separate from the second group 418B of four electrode elements 402E-402H by a distance 420. The distance 420 is greater than a spacing between any two of the four electrode elements 402A-402D the first group 418A and greater than a spacing between any two of the four electrode elements 402E-402H in the second group 418B. That is, the distance 420 is greater than the distance 414 and greater than the distance 416 in the first group 418A of four electrode elements 402A-402D. Similarly, the distance 420 is greater than the corresponding distances in the second group 418B of four electrode elements 402E-402H. Having a larger space between the two groups 418A and 418B of electrode elements than between the individual electrode elements in the groups may help balance the current flowing through the array as follows. Separating the more centrally positioned electrode elements 402B, 402D, 402E, and 402G from each other and leaving a larger space in the middle of the array decreases the amount of shielding experienced by the centrally positioned electrode elements 402B, 402D, 402E, and 402G so that these electrode elements behave more like edge electrode elements (e.g., 402A, 402C, 402F, 402H). Thus, the current through the center portion of the electrode element array may be increased or maximized, and the current through the entire array may be balanced to reduce the edge effect.

As illustrated, the distance 420 between the two groups 418A and 418B of electrodes may be in a direction (e.g., parallel to the Y-axis, as the axes are shown in the Figure) of the longest dimension of the transducer 400/500. In embodiments in which the electrode elements 402 are rectangular or substantially rectangular with one or more rounded edges, as shown, each electrode element 402 may be oriented with its longest dimension substantially perpendicular to the direction of the distance 420 between the groups 418A and 418B. This arrangement may further balance the current output through the array of electrode elements 402 on the transducer 400/500.

In an example, as depicted in FIG. 5, the first group 418A of electrode elements 402A-402D may include two pairs 502A and 502B of electrode elements, the two pairs 502A and 502B of electrode elements being spaced apart (by distance 416) from each other in a second direction (parallel to the X-axis, as the axes are shown in the Figure). The second group 418B of electrode elements 402E-402H may similarly include two pairs 502C and 502D of electrode elements, the two pairs 502C and 502D of electrode elements being spaced apart (by distance 416) from each other in the second direction.

Any number of electrode elements 402 in the array may have substantially similar shapes. For example, in FIGS. 4 and 5, all electrode elements 402A-402H have substantially similar shapes as described above. In other embodiments, one or more electrode elements in the array may have substantially different shapes from one another. As depicted in FIGS. 4 and 5, each electrode element 402A-402H in the array may have approximately the same surface area, further balancing the current output from individual electrode elements.

The PCB layer 405 may include an electrical connector portion 422 that provides a point for connecting leads to the transducer 400/500. In FIG. 4, the electrical connector portion 422 may be disposed at a center portion of the transducer 400 in the space provided by the increased distance 420 between the two groups 418A and 418B of electrode elements. In FIG. 5, at least a portion of the electrical connector portion 422 may be located in the array between two pairs (e.g., 502A and 502B) of electrode elements in one of the groups (e.g., 418A) of four electrode elements (e.g., 402A-402D). The positioning of the electrical connector portion 422 in FIGS. 4 and 5 helps to not break the symmetry of the layout of the electrode element array.

Figure 6A:
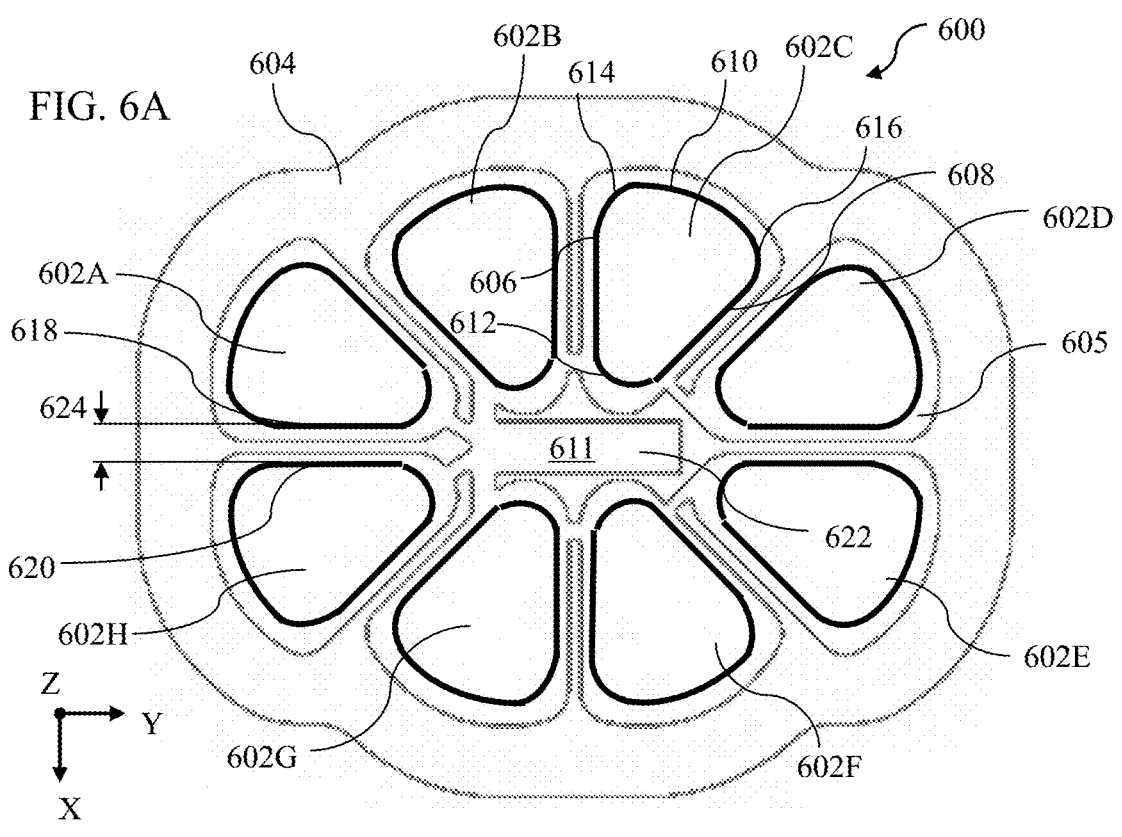
FIGS. 6A and 6B depict another example layout of an array of electrode elements on a transducer apparatus.
Figure 6B:
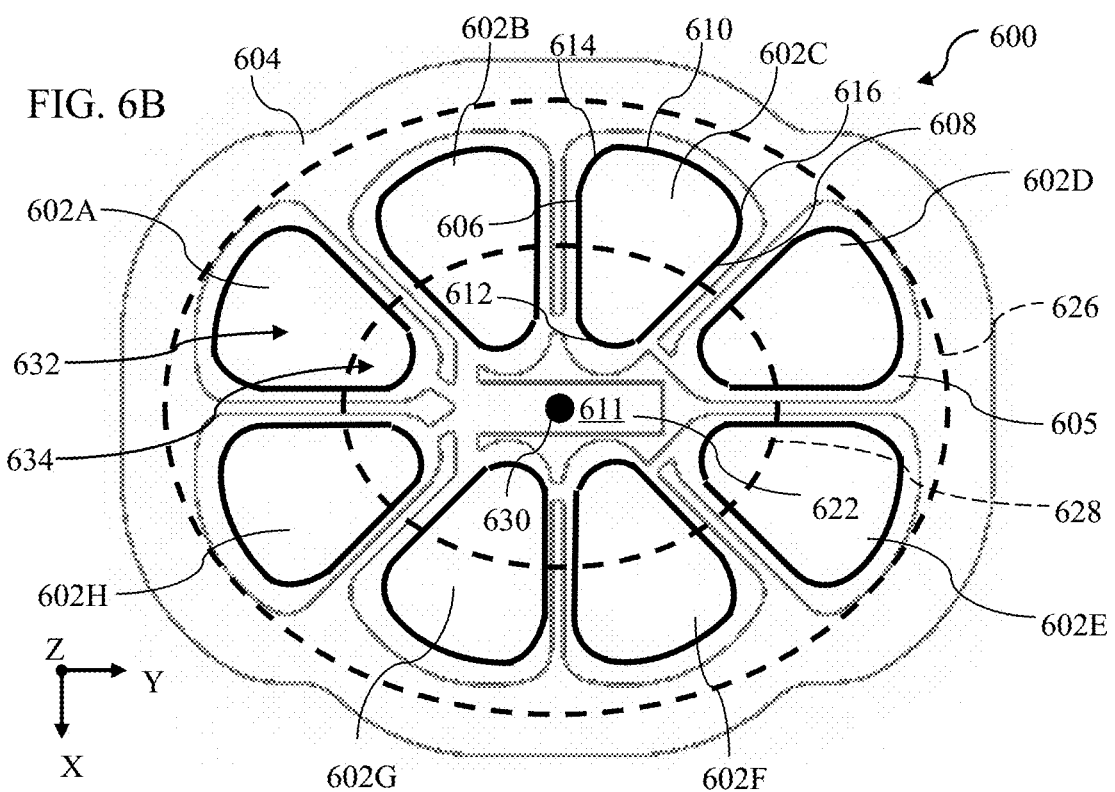
Figure 7:
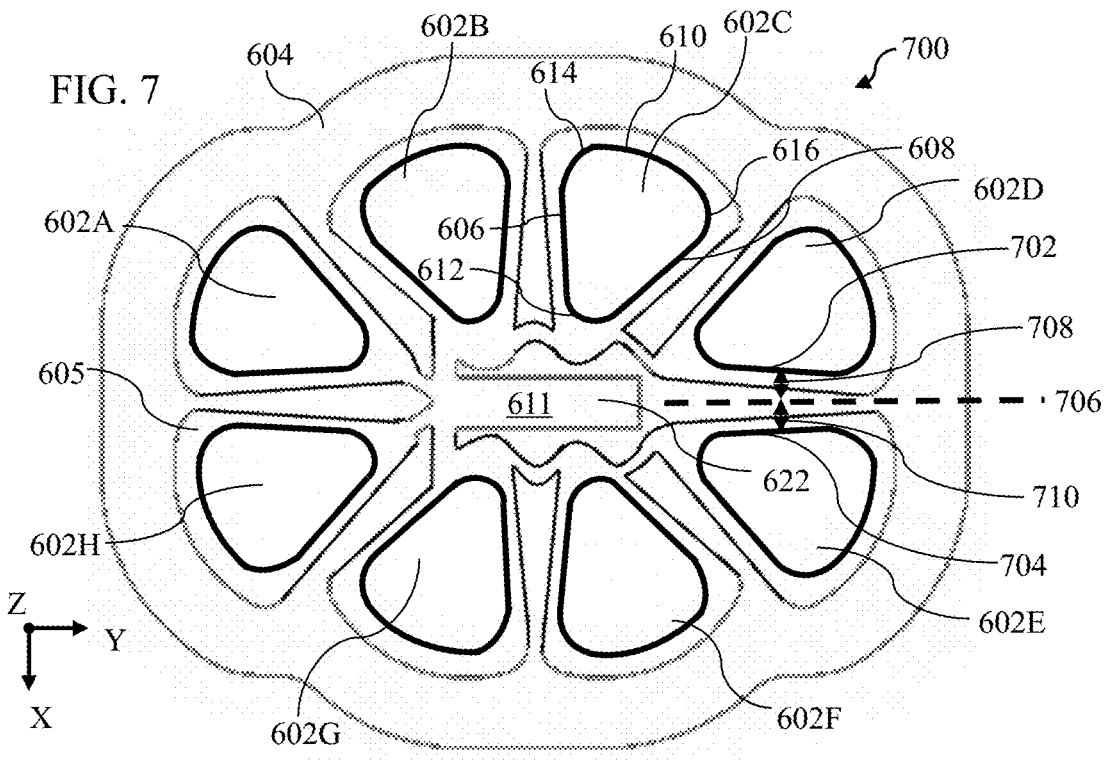
FIG. 7 depicts another example layout of an array of electrode elements on a transducer apparatus.
Figure 8:
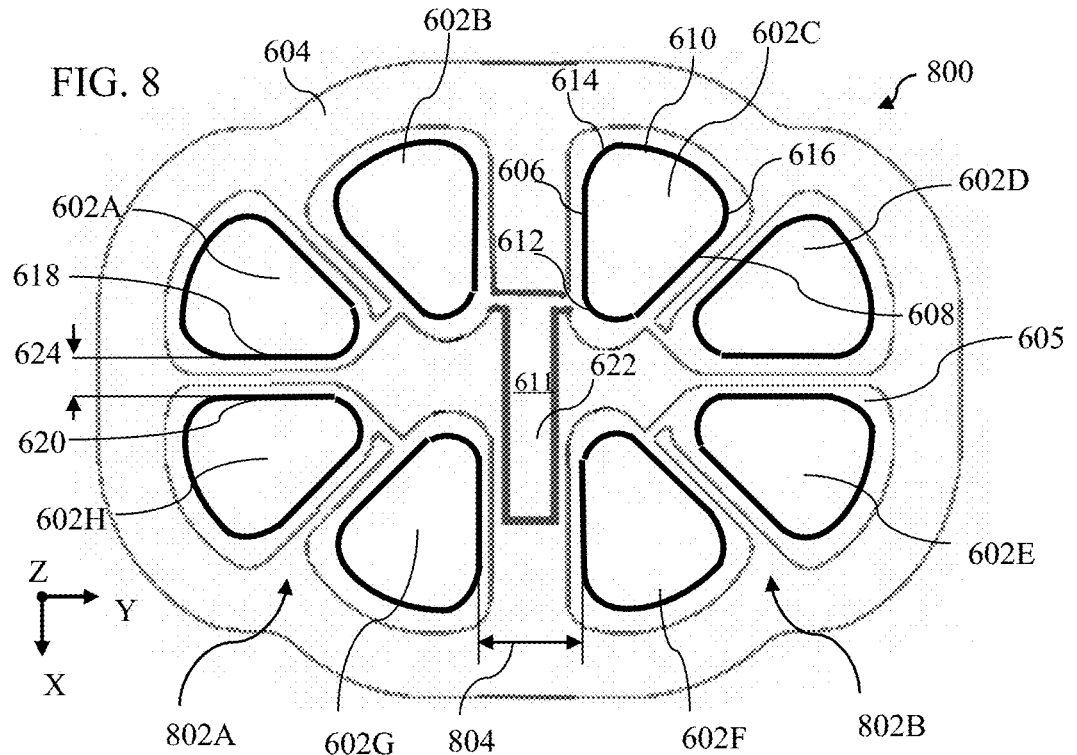
FIG. 8 depicts another example layout of an array of electrode elements on a transducer apparatus.

FIGS. 6A and 6B depict a transducer 600 with an example layout of electrode elements 602 (602A-602H), which may be disposed on a substrate 604. The layout of electrode elements 602 is the same in both FIGS. 6A and 6B. FIGS. 7 and 8 depict transducers 700 and 800 having the same type of electrode elements 602 (602A-602H) but with different shapes and arrangements thereof. As shown in FIGS. 6A-8, the transducers 600, 700, and 800 may each include a PCB layer 605 between the electrode elements 602 and the substrate 604. The PCB layer 605 may include conductive pathways that electrically couple the electrode elements 602 together. The PCB layer 605 may include an electrical connector portion 622 that provides a point for connecting leads to the transducer 600/700/800. As illustrated, the electrical connector portion 622 may be disposed at a center portion 611 of the transducer 600/700/800, surrounded by the electrode elements 602 of the array. Other embodiments of the transducer may feature an electrical connector portion that is located elsewhere on the transducer.

Certain shapes of the individual electrode elements 602 may help balance the current through the array. In an example, at least one of the electrode elements 602 in the array may have a triangular shape, a substantially triangular shape with rounded corners, a truncated triangular shape, a substantially truncated triangular shape with rounded corners, a wedge shape, a substantially wedge shape with rounded corners, a truncated wedge shape, or a substantially truncated wedge shape with rounded corners. FIGS. 6A-8 depicts each of the electrode elements 602 having a substantially wedge shape with rounded corners and a radially external facing rounded edge. As illustrated, the electrode elements 602 are non-circular.

As illustrated with reference to the electrode element 602C, one or more electrode elements 602 may comprise: a first edge 606, a second edge 608, and at least one rounded edge 610 connecting the first edge 606 to the second edge 608 at an end of the electrode element 602C. In FIGS. 6A-8, the first edge 606 and the second edge 608 of the electrode element 602C are not substantially parallel. Rather, the first edge 606 extends in a radially outward direction relative to a center portion 611 of the array, and the second edge 608 extends in a radially outward direction relative to the center portion 611 of the array. The rounded edge 610 connecting the first edge 606 to the second edge 608 is at an end of the electrode element located radially away from the center portion 611 of the array. As illustrated, a rounded corner 612 may connect the first edge 606 to the second edge 608 at an opposite end of the electrode element located radially toward the center portion 611. The radius of curvature of the rounded edge 610 may be larger than the radius of curvature of the rounded corner 612. As illustrated, a rounded corner 614 may connect the first edge 606 to the rounded edge 610 and a rounded corner 616 may connect the second edge 608 to the rounded edge 610.

As depicted in FIGS. 6A and 8, a first electrode element (e.g., 602A) and a second electrode element (e.g., 602H) each have edges located adjacent each other without any other electrodes between them. For example, an edge 618 of the electrode element 602A is located adjacent an edge 620 of the electrode element 602H. Both edges 618 and 620 may be substantially straight edges located between two rounded corners of their respective electrode elements 602A and 602H. As depicted, the edges 618 and 620 extend parallel to each other along their length. Thus, the electrode elements

602A and 602H have a uniform distance 624 therebetween along the length of these opposing edges 618 and 620.

The edge 618 may have a length that is greater than 5% of a total perimeter of the electrode element 602A. More particularly, the edge 618 may have a length that is greater than 10%, greater than 20%, or greater than 25% of the perimeter of the electrode element 602A. Similarly, the edge 620 may have a length that is greater than 5% of the perimeter of the electrode element 602H. More particularly, the edge 620 may have a length that is greater than 10%, greater than 20%, or greater than 25% of the perimeter of the electrode element 602H.

As depicted, an electrode element (e.g., 602A) may have multiple edges that are each parallel to a different adjacent electrode element (e.g., 602H and 602B). For example, in FIGS. 6A, 6B, and 8, the electrode element 602A has another substantially straight edge that is parallel to and located a uniform distance from a substantially straight edge of the electrode element 602B. In the illustrated example, the distance between edges of the electrode elements 602A and 602B may be equivalent to the distance 624 between edges of the electrode elements 602A and 602H. In another example, the distances may be different.

As depicted in FIGS. 6A-8, multiple electrode elements 602 may be arranged peripherally about the center portion 611 of the array. At least one of the electrode elements 602 in the array may extend from the center portion 611 toward an outer periphery of the array. In FIGS. 6A-8, for example, all electrode elements 602A-602H extend from the center portion 611 toward the outer periphery of the array. The peripheral arrangement of the electrode elements 602 may provide additional balance between current output through the electrode elements 602.

FIG. 6B illustrates the transducer 600 having a plurality of electrode elements 602 (602A-602H) and with two illustrative boundaries 626 and 628 drawn over the transducer 600. A first boundary 626 is defined by tracing an outer periphery of the transducer 600. The outer periphery of the transducer 600 may be defined as any one of: a peripheral edge of the PCB layer 605, as shown; a peripheral edge of the substrate 604; or the outer edges of each electrode element 602. The second boundary 628 is defined by continuously tracing a midpoint between the centroid 630 of the transducer 600 and the outer periphery of the transducer at all locations surrounding the centroid 630. For at least one of the electrode elements (e.g., 602A) in the array, a first portion 632 of the electrode element 602A is located inside the first boundary 626 and outside the second boundary 628, a second portion 634 of the electrode element 602A is located inside the second boundary 628, and the area of the first portion 632 is larger than the area of the second portion 634. As such, the largest surface area portion of the electrode element 602A is located closer to the peripheral or exterior edge of the electrode element array, while a smaller surface area portion of the electrode element 602A is located closer to the centroid 630 of the array. In the illustrated embodiment, every electrode element 602 in the array has a greater surface area on the peripheral edge and a smaller surface area toward the centroid 630. FIGS. 7 and 8 have similar spatial configurations of the electrode elements 602 as well.

This spatial configuration of the electrode element 602 with respect to the transducer 600 may improve balancing of heat output from the array. Heat output by an electrode element 602 is a function of current concentration divided by surface area. Higher concentrations of current move through the peripheral portions 632 of the electrode elements 602 than through the inner portions 634 due to shielding from other electrode elements and the edge effect of the array. As such, configuring the electrode element 602 to have an inner portion 634 with a relatively smaller surface area and the peripheral portion 632 with a relatively larger surface area helps balance the amount of heat output from the different portions of the electrode element 602.

FIG. 7 depicts another example of a transducer 700 with an example layout of electrode elements 602 (602A-602H), which may be disposed on the substrate 604. In the transducer 700, the distance between edges of adjacent electrode elements change along the length of the edges. For example, a first electrode element (e.g., 602D) and a second electrode element (e.g., 602E) each have edges located proximate each other without any other electrodes between them. For example, an edge 702 of the electrode element 602D is located adjacent an edge 704 of the electrode element 602E. Both edges 702 and 704 may be substantially straight edges located between two rounded corners of their respective electrode elements 602D and 602E. A distance from the first edge 702 to the second edge 704 changes along a length of the first and second edges 702, 704. Thus, the electrode elements 602D and 602E do not have a uniform distance therebetween along the edges.

In an example, when a bisector 706 is drawn between the first edge 702 and the second edge 704, a distance 708 from the first edge 702 to the bisector 706 measured in a direction perpendicular to the bisector 706 equals a distance 710 from the second edge 704 to the bisector 706 measured in the direction perpendicular to the bisector 706, along the length of the first and second edges 702, 704. In the example of FIG. 7, the first and second edges 702, 704 are both linear. As such, the distance between the first edge 702 and the second edge 704 may have a constant rate of change along the lengths of the edges 702, 704. The first and second edges may be non-linear in other embodiments.

As depicted in FIG. 7, the distance from the first edge 702 to the second edge 704 may decrease along the length of the first and second edges 702, 704 from the central portion 611 toward the outer periphery of the transducer 700. This may improve the balance between heat output from the electrode elements 602, since increasing the distance between electrode elements 602 toward the center will decrease the surface area of the internal portion of the electrode element 602 and thus increase the heat output from this lower current zone.

FIG. 8 depicts an example of a transducer 800 in which the electrode elements 602 (602A-602H) are divided into two groups and the electrical connector portion 622 is aligned in a direction parallel to the X-axis while the largest dimension of the transducer 800 is in a direction parallel to the Y-axis (as the axes are shown in the Figure). In FIG. 8, the transducer 800 includes a first group 802A of electrode elements 602A, 602B, 602G, and 602H and a second group 802B of electrode elements 602C, 602D, 602E, and 602F. As illustrated, the first group 802A of electrode elements is separated from the second group 802B of electrode elements by a distance 804. The distance 804 may be greater than a spacing between any two adjacent electrode elements 602A, 602B, 602G, and 602H in the first group 802A and greater than a spacing between any two adjacent electrode elements 602C, 602D, 602E, and 602F in the second group 802B. That is, the distance 804 may be greater than the distance 624 and greater than the distance between the adjacent electrode elements 602 in either group 802A or 802B. The positioning of the electrode elements 602 and the electrical connector portion 622 of the PCB layer 605 in FIG. 8 may help to improve current or heat balancing between the electrodes while not breaking the symmetry of the electrode layout.

Figure 9:
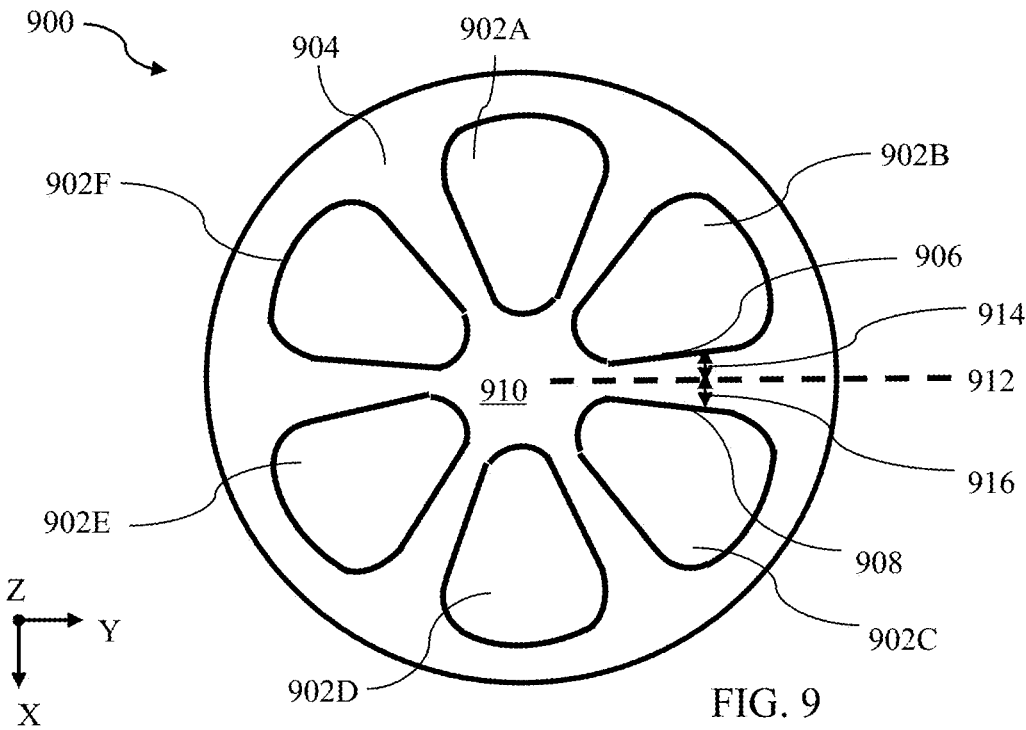
FIG. 9 depicts another example layout of an array of electrode elements on a transducer apparatus.

FIG. 9 depicts another example of a transducer 900 with an example layout of electrode elements 902, which may be disposed on a substrate 904. The transducer 900 may include six electrode elements 902A-902F. In the transducer 900, the shape, size, and overall layout of electrode elements 902 is similar to those of FIG. 7, but with the distance between edges of adjacent electrode elements 902 changing in the opposite direction along the length of the edges. For example, in FIG. 9, an edge 906 of the electrode element 902B is located adjacent an edge 908 of the electrode element 902C. A distance from the first edge 906 to the second edge 908 changes along a length of the first and second edges 906, 908. Thus, the electrode elements 902B and 902C do not have a uniform distance therebetween along the edges. In an example, when a bisector 912 is drawn between the first edge 906 and the second edge 908, a distance 914 from the first edge 906 to the bisector 912 measured in a direction perpendicular to the bisector 912 equals a distance 916 from the second edge 908 to the bisector 912 measured in the direction perpendicular to the bisector 912, along the length of the first and second edges 906, 908. In the example of FIG. 9, the first and second edges 906, 908 are both linear. As such, the distance between the first edge 906 and the second edge 908 may have a constant rate of change along the lengths of the edges 906, 908. In FIG. 9, the distance from the first edge 906 to the second edge 908 may increase along the length of the first and second edges 906, 908 from the central portion 910 toward the outer periphery of the transducer 900. This may improve the balance between heat output from the electrode elements 902 in certain embodiments. The spacing between adjacent electrode elements of the transducers described herein may be adjusted to meet a desired current distribution or heat distribution.

Figure 10:
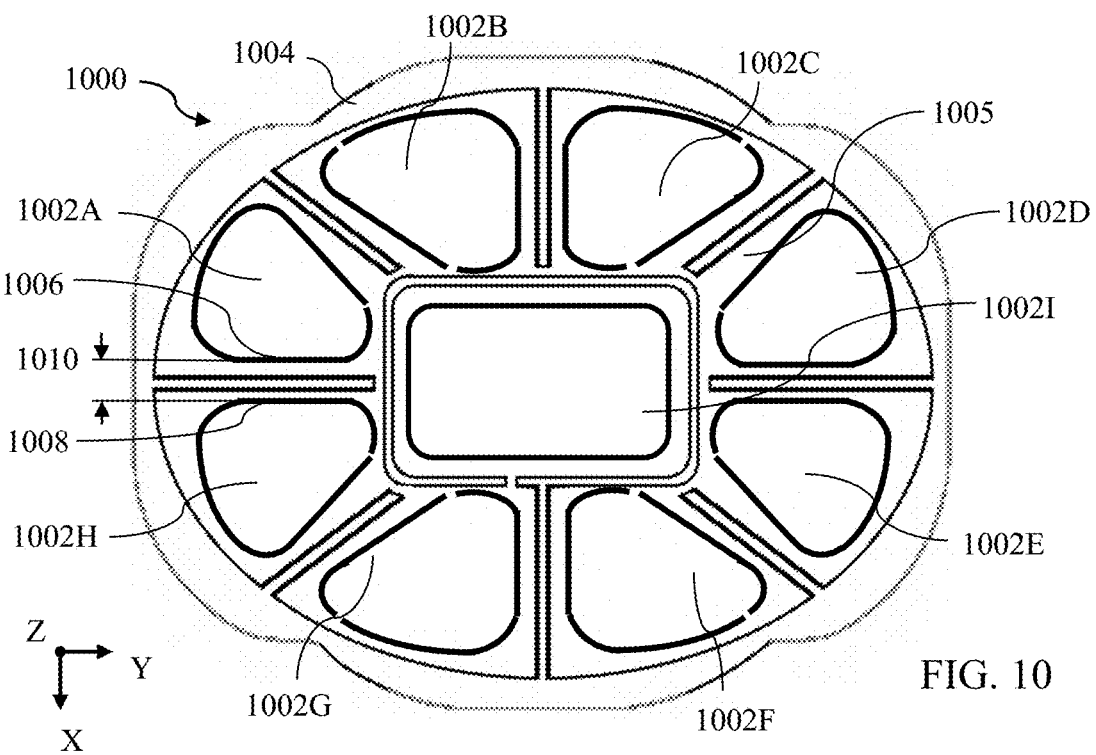
FIG. 10 depicts another example layout of an array of electrode elements on a transducer apparatus.

FIG. 10 depicts another example of a transducer 1000 with an example layout of electrode elements 1002, which may be disposed on a substrate 1004. The transducer 1000 may include nine electrode elements 1002A-1002I, eight of which are peripheral electrode elements 1002A-1002H surrounding a single non-peripheral electrode 1002I. In the transducer 1000, the shape of the peripheral electrode elements 1002A-1002H is similar to the shape of the electrode elements 602A-602H of FIGS. 6A-8. The transducer 1000 may include a PCB layer 1005 between the electrode elements 1002 and the substrate 1004.

As illustrated in FIG. 10, the transducer 1000 may include at least one pair of electrode elements (e.g., 1002A and 1002H) having adjacent edges 1006 and 1008 that are parallel to each other (with a uniform distance 1010). The transducer 1000 may also include at least one pair of electrode elements (e.g., 1002A and 1002B) having adjacent edges that are not parallel to each other and instead have a changing distance therebetween. The electrode elements may, or may not, all have equal sizes and/or shapes. As illustrated in FIG. 10, the transducer 1000 may include an array of electrode elements 1002 that are not all equal sizes or shapes. For example, the non-peripheral electrode element 1002I has a substantially rectangular shape with rounded corners, while each peripheral electrode element 1002A-1002H has a substantially truncated wedge shape with rounded corners and a rounded peripheral edge.

Figure 11:
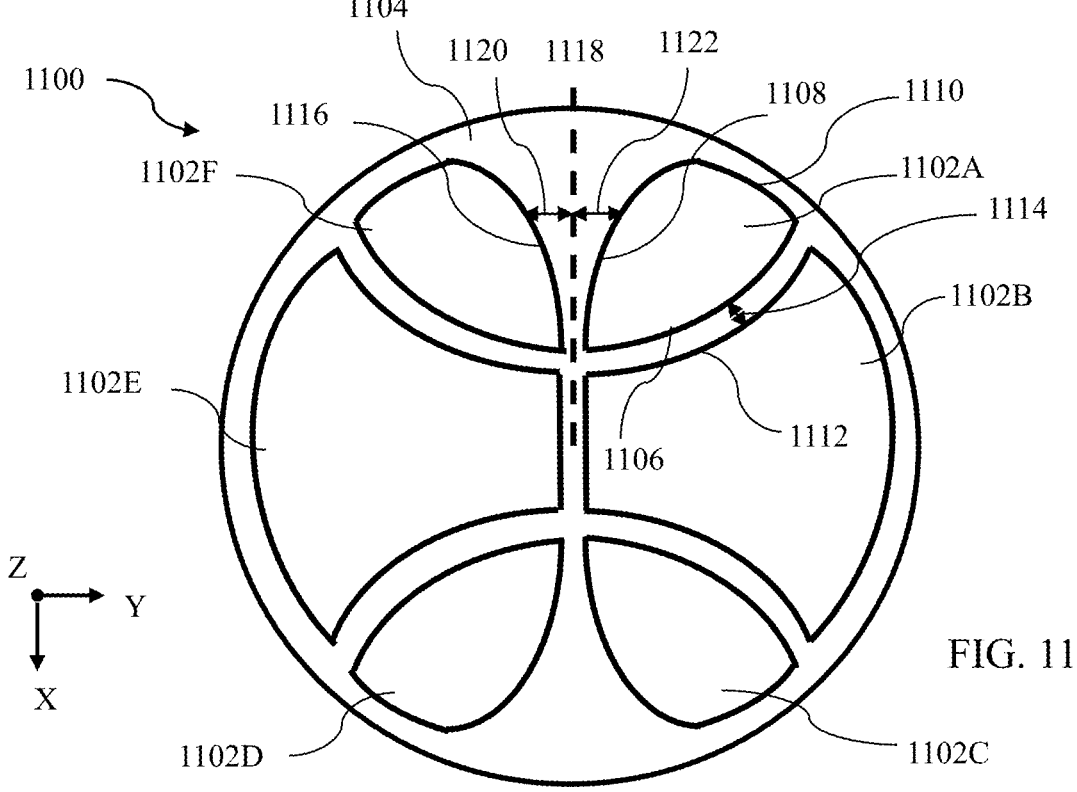
FIG. 11 depicts another example layout of an array of electrode elements on a transducer apparatus.

FIG. 11 depicts a transducer 1100 with an example layout of electrode elements 1102, which may be disposed on a substrate 1104. In FIG. 11, an array of electrode elements comprises six electrode elements 1102A-1102F. In an example, at least one of the electrode elements 1102 in the array may have an irregular shape. FIG. 11 depicts each of the electrode elements 1102 having irregular shapes with one or more edges. As illustrated with reference to the electrode element 1102A, one or more electrode elements 1102 may comprise: a first edge 1106, a second edge 1108, and at least one rounded edge 1110 connecting the first edge 1106 to the second edge 1108 at an end of the electrode element 1102A. In FIG. 11, the first edge 1106 and the second edge 1108 are not substantially parallel. The first edge 1106 and the second edge 1108 both extend in radially outward directions relative to a center portion of the array, and the rounded edge 1110 connects the first edge 1106 to the second edge 1108 at an end of the electrode element located radially away from the center portion of the array.

In an example, the first edge 1106 of the electrode element 1102A is located adjacent an edge 1112 of the electrode element 1102B. The first edge 1106, as shown, may include a curved portion of the electrode element 1102A. Similarly, the edge 1112 of the second electrode element 1102B may include a curved portion of the electrode element 1102B. As depicted, the edge 1106 of the first electrode element 1102A and the edge 1112 of the second electrode element 1102B extend parallel to each other along their length. That is, the electrode elements 1102A and 1102B have a uniform distance 1114 therebetween along the length of these opposing edges 1106 and 1112. Although FIG. 11 shows the edges 1106 and 1112 as each having a curved portion, it should be noted that in other embodiments the edges 1106 and 1112 may have corner portions, zig-zag portions, or other non-linear orientations while remaining equidistant from each other (i.e., substantially parallel along their lengths).

As depicted, the edge 1106 of the electrode element 1102A may have a length that is greater than 5% of a total perimeter of the electrode element 1102A. More particularly, the edge 1106 may have a length that is greater than 10%, greater than 20%, or greater than 25% of the perimeter of the electrode element 1102A. Similarly, the edge 1112 of the electrode element 1102B may have a length that is greater than 5% of the perimeter of the electrode element 1102B. More particularly, the edge 1112 may have a length that is greater than 10%, greater than 20%, or greater than 25% of the perimeter of the electrode element 1102B.

In FIG. 11, an electrode element (e.g., 1102A) and an adjacent electrode element (e.g., 1102F) each have edges located proximate each other. For example, the edge 1108 (referred to hereinafter as the "first edge") of the electrode element 1102A is located adjacent an edge 1116 (referred to hereinafter as the "second edge") of the electrode element 1102F. Both edges 1108 and 1116 may be curved edges. A distance from the first edge 1108 to the second edge 1116 changes along a length of the edges. Thus, the electrode elements 1102A and 1102F do not have a uniform distance therebetween along the edges.

As depicted, when a bisector 1118 is drawn between the first edge 1108 and the second edge 1116, a distance 1120 from the first edge 1108 to the bisector 1118 measured in a direction perpendicular to the bisector 1118 equals a distance 1122 from the second edge 1116 to the bisector 1118 measured in the direction perpendicular to the bisector 1118, along the length of the first and second edges 1108, 1116. In FIG. 11, the first and second edges 1108, 1116 are both non-linear, and therefore the distance between the first edge 1108 and the second edge 1116 does not have a constant rate of change. As depicted in FIG. 11, the distance from the first edge 1108 to the second edge 1116 may increase along the length of the first and second edges 1108, 1116 from the central portion toward the outer periphery of the transducer 1100. In other embodiments, the distance between two curved edges may decrease from the central portion toward the outer periphery of the transducer.

The invention includes other items, such as the following.

Item 1. A transducer apparatus for delivering tumor treating fields to a subject's body, the transducer apparatus comprising: a plurality of electrode elements; wherein the plurality of electrode elements comprises a first electrode element and a second electrode element, wherein the first electrode element and the second electrode element are substantially located in a plane of the transducer apparatus; and when viewed from a direction perpendicular to the plane, the first electrode element and the second electrode element have edges located adjacent each other without any other electrodes between them, wherein the edges of the first electrode element and the second electrode element extend parallel to each other along their length.

Item 2. The transducer apparatus of Item 1, wherein at least one of the electrode elements in the array has an irregular shape.

Item 3. The transducer apparatus of Item 1, wherein the electrode elements comprise polymer films disposed over pads on a printed circuit board or over substantially planar metal.

Item 4. A transducer apparatus for delivering tumor treating fields to a subject's body, the transducer apparatus comprising: a first electrode element having a first edge; a second electrode element electrically coupled to the first electrode element, the second electrode element having a second edge; wherein the first electrode element and the second electrode element are substantially located in a plane of the transducer apparatus; and when viewed from a direction perpendicular to the plane, the first edge is located proximate to the second edge; and a distance from the first edge to the second edge changes along a length of the first and second edges, wherein the first electrode element and the second electrode element are non-circular.

Item 5. The transducer of Item 4, wherein at least one of the first edge and the second edge is non-linear.

Item 6. A transducer apparatus for delivering tumor treating fields to a subject's body, the transducer apparatus comprising: an array of eight electrode elements, the array configured to be positioned over the subject's body with a face of the array facing the subject's body; wherein, when viewed from a direction perpendicular to the face of the array, each electrode element has a substantially square, rectangular, or hexagonal shape or a substantially square, rectangular, or hexagonal shape with rounded corners, and the eight electrode elements include a first group of four electrode elements arranged in a 2×2 grid pattern and a second group of four electrode elements arranged in a 2×2 grid pattern; wherein the first group of four electrode elements is separated from the second group of four electrode elements by a distance that is greater than a spacing between any two of the four electrode elements in the first group and greater than a spacing between any two of the four electrode elements in the second group.

Item 7. The transducer apparatus of Item 6, wherein, when viewed from the direction perpendicular to the face of the array: the first group of electrode elements is separated from the second group of four electrode elements in a first direction; the first group of four electrode elements includes two pairs of electrode elements, the two pairs being spaced apart from each other in a second direction perpendicular to the first direction; and the second group of four electrode elements includes two pairs of electrode elements, the two pairs being spaced apart from each other in the second direction.

Item 8. A transducer apparatus for delivering tumor treating fields to a subject's body, the transducer apparatus comprising: an array of multiple electrode elements, the array configured to be positioned over the subject's body with a face of the array facing the subject's body; wherein, when viewed from a direction perpendicular to the face of the array, at least one electrode element is located proximate a center portion of the array, the at least one electrode element comprising: a first edge extending in a radially outward direction relative to the center portion of the array; a second edge extending in a radially outward direction relative to the center portion of the array; and a rounded edge connecting the first edge to the second edge at an end of the electrode element located radially away from the center portion of the array.

Item 9. A transducer apparatus for delivering tumor treating fields to a subject's body, the transducer apparatus comprising: a plurality of electrode elements, wherein the plurality of electrode elements comprises a first electrode element substantially located in a plane of the transducer apparatus; and when viewed from a direction perpendicular to the plane, a first boundary is defined by tracing an outer periphery of the transducer apparatus; a second boundary is defined by continuously tracing a midpoint between the centroid of the transducer apparatus and the outer periphery of the transducer apparatus at all locations surrounding the centroid; a first portion of the first electrode element is located inside the first boundary and outside the second boundary; a second portion of the first electrode element is located inside the second boundary; and the area of the first portion is larger than the area of the second portion.

Item 10. A transducer apparatus according to Item 9, wherein the plurality of electrode elements further comprises a second electrode element, the first electrode element and the second electrode element have edges located adjacent each other without any other electrodes between them, and the edges of the first electrode element and the second electrode element extend parallel to each other along their length.

Item 11. A transducer apparatus according to Item 9, wherein the first electrode element comprises: a first edge extending in a radially outward direction relative to the centroid; a second edge extending in a radially outward direction relative to the centroid; and a rounded edge connecting the first edge to the second edge at an end of the electrode element located radially away from the centroid.

Item 12. A transducer apparatus according to Items 1, 4, 6, 8 or 9, wherein each electrode element has approximately the same surface area.

Item 13. A transducer apparatus according to Item 6, further comprising an electrical connector coupled to the array of eight electrode elements, wherein the electrical connector is located in the array between the first group of four electrode elements and the second group of four electrode elements.

Item 14. A transducer apparatus according to Item 7, further comprising an electrical connector coupled to the array of eight electrode elements, wherein at least a portion of the electrical connector is located in the array between the two pairs of electrode elements in the first group of four electrode elements.

Item 15. A transducer apparatus according to Item 8, further comprising an electrical connector coupled to the array of electrode elements, wherein the electrical connector is located in the center portion of the array.

Item 16. A transducer apparatus according to Item 8, wherein the multiple electrode elements include a first group of electrode elements and a second group of electrode elements, wherein when viewed in the direction perpendicular to the face of the array, the first group of electrode elements is separated from the second group of electrode elements by a distance that is greater than a spacing between any two adjacent electrode elements in the first group and greater than a spacing between any two adjacent electrode elements in the second group.

For each embodiment disclosed herein, an edge of a first electrode element may have a length that is greater than 5% of a total perimeter of the first electrode element; in particular, an edge of a first electrode element may have a length that is greater than 10%, greater than 20%, or greater than 25% of the perimeter of the first electrode element; and an edge of a second electrode element may have a length that is greater than 5% of the perimeter of the second electrode element; in particular, an edge of the second electrode element may have a length that is greater than 10%, greater than 20%, or greater than 25% of the perimeter of the second electrode element.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A transducer apparatus configured to deliver tumor treating fields having a frequency from 50 kHz to 1 MHz to a subject's body, the transducer apparatus comprising:
   an array of a plurality of electrode elements, wherein the plurality of electrode elements is capable of delivering tumor treating fields to the subject's body;
   wherein the plurality of electrode elements comprises a first electrode element and a second electrode element, wherein the first electrode element and the second electrode element are substantially located in a plane of the transducer apparatus; and
   when viewed from a direction perpendicular to the plane, the first electrode element and the second electrode element have edges located adjacent each other without any other electrodes between them, wherein the edges of the first electrode element and the second electrode element extend parallel to each other along their length, and each of the edges is a substantially straight edge portion located between two rounded corners of the corresponding electrode element.

2. The transducer apparatus of claim 1, wherein each of the edges has a curved, corner, or zig-zag portion, wherein the curved, corner, or zig-zag portions of the edges are non-linear, and wherein the edges are equidistant from each other along the length of the curved, corner, or zig-zag portions.

3. The transducer apparatus of claim 1, wherein the edge of the first electrode element has a length greater than 5% of the perimeter of the first electrode element, and the edge of the second electrode element has a length greater than 5% of the perimeter of the second electrode element.

4. The transducer apparatus of claim 1, wherein at least one of the electrode elements in the array has a square, rectangular, or hexagonal shape or a substantially square, rectangular, or hexagonal shape with one or more rounded corners; or at least one of the electrode elements in the array has a triangular shape, a substantially triangular shape with rounded corners, a truncated triangular shape, a substantially truncated triangular shape with rounded corners, a wedge shape, a substantially wedge shape with rounded corners, a truncated wedge shape, or a substantially truncated wedge shape with rounded corners.

5. The transducer apparatus of claim 1, wherein the first electrode element has:

a second edge; and at least one rounded edge connecting the edge of the first electrode element to the second edge at an end of the first electrode element.

6. The transducer apparatus of claim 5, wherein the edge and the second edge of the first electrode element are substantially parallel.

7. The transducer apparatus of claim 5, wherein the edge and the second edge of the first electrode element are not substantially parallel.

8. The transducer apparatus of claim 1, wherein at least one of the electrode elements in the array is extending from a central portion of the array toward an outer periphery of the array.

9. The transducer apparatus of claim 1, wherein the electrode elements are (i) capacitively coupled or (ii) not capacitively coupled.

10. The transducer apparatus of claim 1, wherein the electrode elements are electrically coupled together.

11. A transducer apparatus configured to deliver tumor treating fields having a frequency from 50 kHz to 1 MHz to a subject's body, the transducer apparatus comprising:

an array of multiple electrode elements, the array configured to be positioned over the subject's body with a face of the array facing the subject's body, the array capable of delivering tumor treating fields to the subject's body;

wherein, when viewed from a direction perpendicular to the face of the array, at least one electrode element is located proximate a center portion of the array, the at least one electrode element comprising:

a first edge extending in a radially outward direction relative to the center portion of the array;

a second edge extending in a radially outward direction relative to the center portion of the array; and a rounded edge connecting the first edge to the second edge at an end of the respective electrode element located radially away from the center portion of the array.

12. The transducer apparatus of claim 11, wherein a distance from the first edge to the second edge decreases toward the outer periphery of the array.

13. The transducer apparatus of claim 11, wherein a distance from the first edge to the second edge increases toward the outer periphery of the array.

14. The transducer apparatus of claim 11, wherein the electrode elements are electrically coupled together.

15. The transducer apparatus of claim 11, wherein the electrode elements are (i) capacitively coupled or (ii) not capacitively coupled.

16. The transducer apparatus of claim 11, wherein the rounded edge is a single rounded edge.

17. A transducer apparatus configured to deliver tumor treating fields having a frequency from 50 kHz to 1 MHz to a subject's body, the transducer apparatus comprising:

an array of multiple electrode elements, the array configured to be positioned over the subject's body with a face of the array facing the subject's body, the array capable of delivering tumor treating fields to the subject's body;

wherein the multiple electrode elements are arranged peripherally about a center portion of the array, and, when viewed from a direction perpendicular to the face of the array, one end of each of the electrode elements is located proximate the center portion of the array, the electrode elements each comprising:

a first edge extending in a radially outward direction relative to the center portion of the array;

a second edge extending in a radially outward direction relative to the center portion of the array; and a rounded edge connecting the first edge to the second edge at an end of the respective electrode element located radially away from the center portion of the array.

18. The transducer apparatus of claim 17, wherein the electrode elements are electrically coupled together.

19. The transducer apparatus of claim 17, wherein the electrode elements are (i) capacitively coupled or (ii) not capacitively coupled.

20. The transducer apparatus of claim 17, wherein the rounded edge is a single rounded edge.

* * * * *